United States Patent
Guay

(10) Patent No.: US 11,647,926 B2
(45) Date of Patent: May 16, 2023

(54) DEVICE FOR MEASURING MUSCLE CONTRACTIONS AND/OR MUSCLE RELAXATION, AND ASSOCIATED METHODS

(71) Applicant: FIZIMED, Strasbourg (FR)

(72) Inventor: Julien Guay, Strasbourg (FR)

(73) Assignee: FIZIMED, Strasbourg (FR)

( * ) Notice: Subject to any disclaimer, the term of this patent is extended or adjusted under 35 U.S.C. 154(b) by 163 days.

(21) Appl. No.: 16/652,303

(22) PCT Filed: Sep. 17, 2018

(86) PCT No.: PCT/FR2018/052267
§ 371 (c)(1),
(2) Date: Mar. 30, 2020

(87) PCT Pub. No.: WO2019/077215
PCT Pub. Date: Apr. 25, 2019

(65) Prior Publication Data
US 2020/0281516 A1    Sep. 10, 2020

(30) Foreign Application Priority Data

Oct. 16, 2017 (FR) .................................. 1759664

(51) Int. Cl.
| | |
|---|---|
| *A61B 5/22* | (2006.01) |
| *A61B 5/11* | (2006.01) |
| *A61B 5/00* | (2006.01) |
| *A63B 23/20* | (2006.01) |
| *A61B 5/03* | (2006.01) |

(52) U.S. Cl.
CPC .............. *A61B 5/227* (2013.01); *A61B 5/036* (2013.01); *A61B 5/1107* (2013.01);
(Continued)

(58) Field of Classification Search
CPC ....... A61B 5/227; A61B 5/036; A61B 5/4337; A61B 5/7405; A61B 5/742;
(Continued)

(56) References Cited

U.S. PATENT DOCUMENTS

| 5,483,832 A | 1/1996 | Pauser et al. | |
|---|---|---|---|
| 6,905,471 B2 * | 6/2005 | Leivseth | A63B 23/20 600/591 |

(Continued)

FOREIGN PATENT DOCUMENTS

| ES | 1162833 U | 8/2016 |
|---|---|---|
| WO | 2011/159906 A2 | 12/2011 |

(Continued)

OTHER PUBLICATIONS

Dec. 12, 2018 International Search Report issued in International Patent Application No. PCT/FR2018/052267.
Oct. 21, 2019 International Preliminary Report on Patentability issued in International Patent Application No. PCT/FR2018/052267.

*Primary Examiner* — Daniel L Cerioni
*Assistant Examiner* — Jonathan E. Cooper
(74) *Attorney, Agent, or Firm* — Oliff PLC

(57) ABSTRACT

A device for measuring contractions and/or relaxation of one or more muscles of a body cavity, the device having a hollow body which is for positioning in the body cavity and which is covered by a coating made of or having a biocompatible material, the body being formed of two half-shells which are each physically connected, permanently and continuously during the use of the device, with the aid of non-compressible or deformable connecting means, to at least one pressure sensor, or part of the pressure sensor, arranged in the body. Also, a method for measuring the contraction and/or relaxation of the muscles of a body cavity, a method for monitoring the contractions and/or relaxation of the muscles, and a method for exercising these muscles.

17 Claims, 2 Drawing Sheets

(52) U.S. Cl.
CPC ............ *A61B 5/4337* (2013.01); *A61B 5/742* (2013.01); *A61B 5/7405* (2013.01); *A63B 23/20* (2013.01); *A61B 2505/09* (2013.01); *A61B 2562/0247* (2013.01)

(58) Field of Classification Search
CPC ........ A61B 2505/09; A61B 2562/0247; A61B 5/224; A61B 5/1107–1108; A61B 5/4306–4368; A61B 5/74–745; A61B 2562/00; A61B 2562/0261; A63B 23/20
USPC ........................................................ 600/591
See application file for complete search history.

(56) References Cited

U.S. PATENT DOCUMENTS

| | | |
|---|---|---|
| 2003/0083590 A1 | 5/2003 | Hochman et al. |
| 2011/0221014 A1* | 9/2011 | Nakatani ............... G01L 9/0042 438/51 |
| 2016/0279469 A1 | 9/2016 | Rose |

FOREIGN PATENT DOCUMENTS

| | | |
|---|---|---|
| WO | 2016/042310 A1 | 3/2016 |
| WO | 2016/202696 A1 | 12/2016 |
| WO | 2016/203485 A1 | 12/2016 |
| WO | 2017-070787 A1 | 5/2017 |

\* cited by examiner

DEVICE FOR MEASURING MUSCLE CONTRACTIONS AND/OR MUSCLE RELAXATION, AND ASSOCIATED METHODS

SUBJECT MATTER OF THE INVENTION

The present invention relates to a device for measuring internal muscle contractions, in particular of the muscles of a body cavity, more specifically of the muscles of the perineum, and a method for monitoring contractions and an exercise method of these muscles, which implements the device.

BACKGROUND OF THE INVENTION

Devices for simulating external muscles, such as the muscles of the arms, thighs or abdominals, are well known. Generally, this involves electrostimulation devices delivering an electric current inducing the contraction of the muscles.

For internal muscles, in particular those belonging to a muscle cavity, particularly for the muscles of the pelvic floor, it is also known to use so-called "active" devices, which cause contractions to exercise and strengthen these muscles. However, so-called "passive" devices also exist that do not stimulate the muscles, but record the natural contractions of the muscles, and lastly, so-called "mixed" devices that combine both electrical stimulation and recording of the contractions.

For example, document WO2011159906 describes an "active" device, for stimulating the perineum, comprising an extensible part, extending using an inflatable balloon, and allowing direct contact of the surface electrodes with a portion of the vaginal wall in order to cause muscle contractions.

Furthermore, document US2003083590 describes an "active" intravaginal probe, for the electrical stimulation of the muscles of the perineum, comprising means for electrical stimulation of the muscles and wireless communication means in order to communicate with a separate control box.

Regarding "passive" devices, document US2016279469 describes a device for exercising the perineum, comprising an ovoid body inserted into the vagina, a tail that extends to the outside and comprising a communication antenna for interaction with an external device of the smartphone type, the two parts being joined by a narrow part comprising anchoring protuberances and a strain gauge for detecting contractions, the gauge being able to extend in the ovoid body and in the tail.

Document WO2016/202696 describes a probe for measuring the strength of the muscles of the pelvic floor, comprising a solid shell, covered by a layer of a biocompatible material, and comprising a plurality of sensor elements and a processing unit, which are embedded in a conductive and deformable polymeric material, the probe having a substantially cylindrical shape, and certain regions of which have diameters with cross-sections of different sizes.

Document U.S. Pat. No. 5,483,832 describes a contraction measuring probe, which is substantially cylindrical, comprising a plurality of deformable cylindrical chambers, positioned concentrically on one another, and connected to a duct filled with a fluid, the duct being connected to a display device.

However, this type of device has the drawback of not being sensitive and only making it possible to detect contractions of the muscles at a very limited area of the body cavity in which these muscles are located.

Document WO2016042310 describes an ovoid device for measuring the contraction of the perineal muscles, comprising a housing comprising a first upper part and a second part comprising a lower part and a central part, a finger protruding inside the housing from the upper part into a guide well of the central part, in order, in response to a force exerted on the upper and/or lower part, to exert pressure on a force sensor positioned in the lower part of the housing.

Nevertheless, this device has the drawback of not being very sensitive, which requires the use of damping means inside the device, positioned between the end of the finger and the force sensor, in order to improve the stability of the measurements. Furthermore, this device is subject to the rotational movement of the upper and lower parts relative to one another, which causes poor positioning of the finger in the well and therefore a lack of reliability of the measurements. This therefore requires the use of a rotation damper, an anti-roll bar, in order to reduce or prevent these untimely movements. Ultimately, such a device is complex to manufacture, unreliable and not very sensitive during contraction measurements.

Among the "mixed" devices, document WO2016203485 discloses a cylindrical device, having a length of 3 to 8 cm and a diameter between 1 and 3 cm, comprising a pressure sensor of the piezoelectric type, positioned at one or both ends of the device in order to detect the radial forces exerted around the circumference of the device, the electric battery, a transmitter to communicate with the receiver and an electronic muscle stimulation system.

Likewise, document WO2017/070787 describes a mixed device, the body of which comprises an internal skeleton comprising an outer surface, covered with an outer layer of non-toxic, flexible material, and forming, with the outer surface of the skeleton, a partially compressible air flow channel in fluid communication with at least one pressure sensor positioned in the body of the device, in order to detect changes in air pressure due to the pressures applied on the outer layer of flexible material.

AIMS OF THE INVENTION

The present invention aims to provide a device for measuring natural contractions, and the relaxation, of muscles of a body cavity and a method for measuring, a method for monitoring, the contractions and the relaxation, and a method for exercising such muscles, that do not have the drawbacks of the state of the art.

The present invention in particular aims to provide a device for measuring natural contractions, and the relaxation, of muscles of a body cavity that has an improved measuring sensitivity, and making it possible to detect the contraction, and also the relaxation, of a muscle irrespective of the location of the body cavity from which it originates.

The present invention also aims to provide a device for measuring natural muscle contractions of a body cavity that is less complex to manufacture.

The present invention also proposes a method for monitoring the contraction, and the relaxation, of the muscles of a body cavity and a method for exercising these muscles, which do not have the drawbacks of the solutions of the state of the art, and which are simple to implement.

BRIEF DESCRIPTION OF THE INVENTION

The present invention relates to a device for measuring contractions and/or the relaxation of one or several muscles of a body cavity, the device comprising a hollow body which is for positioning in said body cavity, and which is covered by a coating made of, or comprising, a biocompatible material, the body being formed by two half-shells which are each physically connected, permanently and continuously during the use of the device, using non-compressible or deformable connecting means, to at least one pressure sensor, or part of the pressure sensor, arranged in said body.

According to preferred embodiments of the invention, the device according to the invention comprises at least one, or any appropriate combination, of the following features:
- the connecting means of the two half-shells to the sensor comprise, or are made up of, at least one screw, preferably two screws, engaging both one of the half-shells and the sensor or a part of said sensor,
- the half-shells are mounted floating relative to one another, the edges of the first half-shell not coming into contact with the edges of the second half-shell, thus creating a space between the two half-shells,
- said device comprises two pressure sensors, each sensor being coupled, by separate connecting means, to a half-shell,
- the pressure sensor(s) is, or are, of the weight indicator type and comprises(s) a body made from aluminum and two strain gauges positioned on two opposite surfaces of the body,
- the device further comprises wireless communication means with an external mobile device,
- wherein the body comprises a first part located, during the use of said device, in the bodily cavity form, which is ovoid, a second part located, during the use of said device, outside the bodily cavity, with a spheroid shape, said first and said second parts being coupled to one another by an intermediate part with a substantially cylindrical shape.

The present invention also relates to a measuring assembly for monitoring contractions and/or the relaxation and exercise of muscles forming, or being comprised in, a bodily cavity, the assembly comprising one or several measuring devices according to the invention and one or several external mobile devices with which the device(s) according to the invention communicate(s).

In the measuring assembly according to the invention, the external mobile device(s) comprise(s) means of communication with the user of the measuring device(s) according to the invention, and optionally also means of communication using a telephone or Internet communication network for communication with a remote third party.

The present invention also relates to a method for measuring the contraction and/or the relaxation of the muscles of a bodily cavity of a user, comprising the steps of taking one or several measuring devices according to the invention, or the measuring assembly according to the invention, starting the measuring device(s), placing the measuring device(s) in a bodily cavity of the user comprising or being formed by muscles, identifying and measuring the amplitude and/or the duration of a first maximal contraction and/or a first maximal relaxation of the muscles, identifying and measuring, over time, the amplitude and/or the duration and/or the frequency of one or several subsequent contractions and/or subsequent relaxations, the amplitude and/or the duration of the first maximal contraction and the amplitude and/or the duration and/or the frequency of the subsequent contraction(s) and/or subsequent relaxations constituting measurement data, and communicating and displaying, in real time, the measurement data to the user.

Preferably, the measuring method according to the invention further comprises a step for communication by the measuring device(s) of its or their operating state and/or a step for calibration of said measuring device(s), before and/or after it or they are placed in the bodily cavity.

The present invention further relates to a method for monitoring the contraction and/or the relaxation of the muscles of a bodily cavity comprising the implementation of the measuring method according to the invention, and a step for comparing measuring data, collected over time using the measuring method according to the invention, with the data of the first maximal contraction and/or the first maximal relaxation, for a same series of measurements, or the comparison with the data of the first maximal contractions and/or maximal relaxations of preceding series of measurements from a measurement history or one or several average values of first maximal contractions and/or maximal relaxations of said preceding measurements.

Preferably, the method for monitoring the contraction of the muscles further comprises a step for communicating, to the user, one or several written, graphic and/or auditory representations of the results from the step for comparison of the data.

The present invention additionally relates to a method for exercising muscles of a bodily cavity comprising implementing the measuring method according to the invention, or the monitoring method according to the invention, and comprises a step for adapting the amplitude and/or the duration and/or the number and/or the frequency of the contractions and/or relaxations done by, or requested from, the user as a function of the data from the first maximal contraction and/or first maximal relaxation and/or the muscle fatigue of the user identified by the monitoring method of the invention.

Preferably, the measuring method according to the invention and/or the monitoring method according to the invention and/or the exercise method according to the invention further comprise(s) a step for communication by the measuring device(s) according to the invention, or the external mobile device, with a third party remote from the user in order to prepare and/or execute one or several steps of the measuring, monitoring and/or exercise methods, or for the communication of indicators representative of the muscle performance of the user.

DETAILED DESCRIPTION OF THE INVENTION

Figure 1:
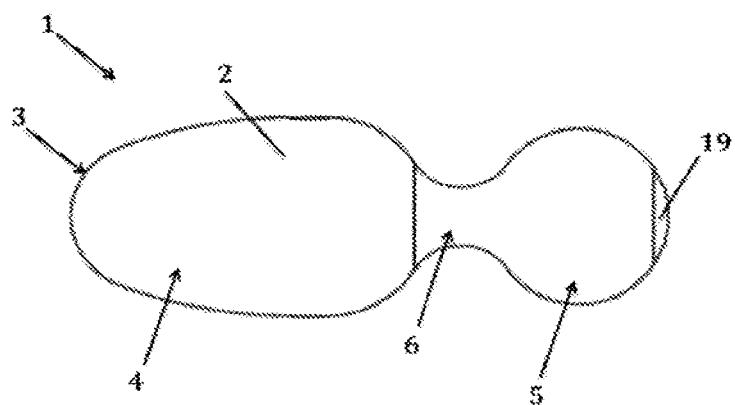
FIG. 1 is a schematic side view of one embodiment of the device according to the invention.
Figure 2:
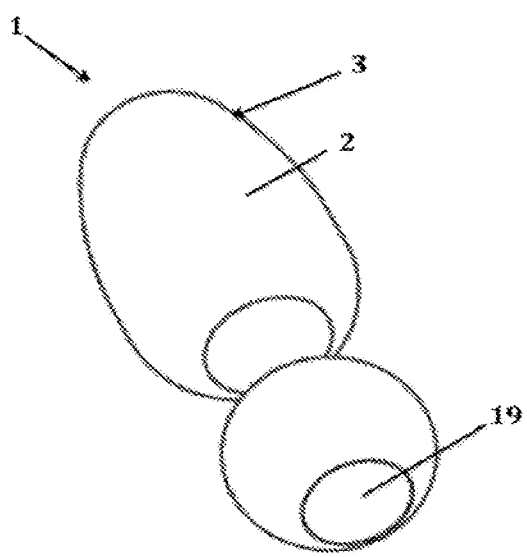
FIG. 2 is a schematic perspective view of the embodiment of the device of FIG. 1.
Figure 3:
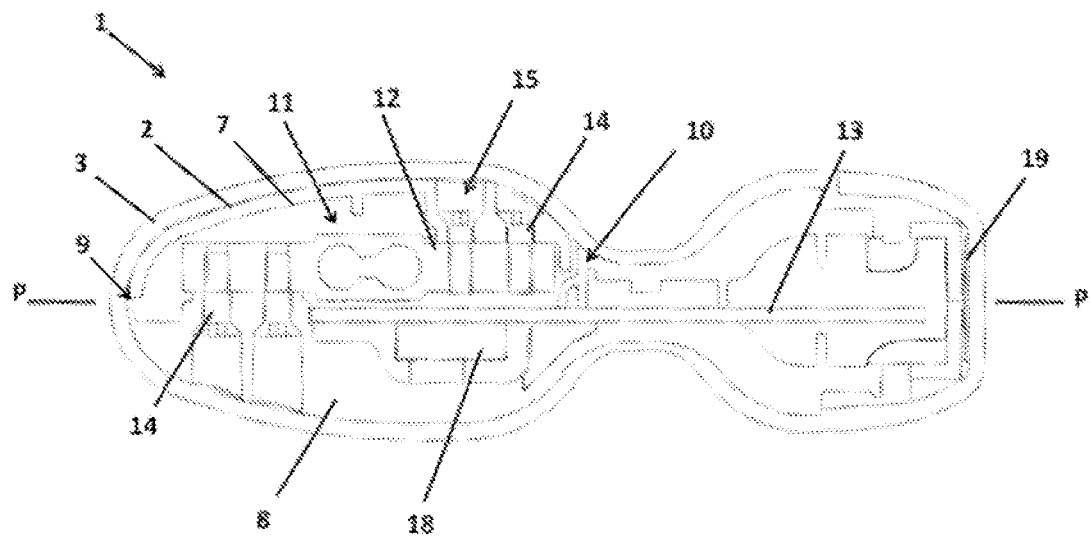
FIG. 3 is a schematic longitudinal sectional view of the embodiment of the device of FIG. 1.

In the remainder of the disclosure and the claims, the terms "top", "bottom", "upper", "lower", "vertical" and "horizontal" refer to the horizontal position of the device 1 according to the invention, as shown in FIGS. 1 and 3.

The device 1 according to the invention is a so-called "passive" probe because it does not stimulate the muscles, but records their natural contractions and/or the muscle relaxation following a contraction, originating from the voluntary stimulation of the muscles by the user of the device 1.

The device 1 comprises a hollow body, preferably made from a rigid material, preferably plastic, and advantageously covered by a material in the form of a coating 3 or a film, made in one piece, or several elements, and made from a material with a base of a biocompatible material, for example with a base of medical-grade silicone. For a coating 3 with several elements, these elements can be joined relative to one another edge to edge, for example using a biocompatible glue, by mechanical fitting or using mechanical joining means, for example clips. Preferably, the junction of the elements makes it possible to guarantee the tightness of the device 1. The coating 3 is preferably smooth and has no unevenness so as to facilitate the cleaning and upkeep of the device 1.

The body 2 of the device 1 has dimensions and a shape that are adapted to and compatible with the bodily cavity or cavities in which it is inserted in order to measure the contraction of the muscle(s) forming, or comprised in, the bodily cavity or cavities.

In the remainder of the disclosure, the device 1 according to the invention will be described for a bodily cavity open to the outside, and as shown in FIGS. 1 to 4. However, the device 1 can be adapted to any possible type and nature of bodily cavity.

Thus, for such a bodily cavity, for example the vagina of a woman or the anal cavity of a woman or a man, the body 2 of the device 1 comprises a first part 4 located, during the use of the device 1, in said bodily cavity and a second part 5 located outside the bodily cavity, these two parts 4 and 5 being coupled to one another by an intermediate part 6 (FIG. 1).

The first part 4 of the device 1 has a shape and sizes that are a function of, and adapted to, the bodily cavity or cavities in which it is intended to be inserted. Preferably, this first part 4 has a substantially cylindrical, spheroid, shape, or is substantially in the shape of a sphere, ovoid or ellipsoid.

The second part 5 of the device 1 has an appropriate shape and dimensions allowing it to be grasped by the user for the placement in, and removal of the device 1 from, the bodily cavity open to the outside. This second part 5 preferably has a spheroid shape, preferably it is substantially in the shape of a sphere, or advantageously an ovoid shape, and can comprise all or some of the components of the device 1.

The intermediate part 6 has any appropriate shape and sizes. Preferably, it is cylindrical, or substantially cylindrical, and forms a narrowing between the first part 4 and the second part 5 of the body 2, which has the advantage of procuring improved comfort during the use of the device 1, in particular regarding the bodily cavity or cavities closed by a sphincter, tissues or muscles, for example the anal or vaginal orifice.

Figure 4:
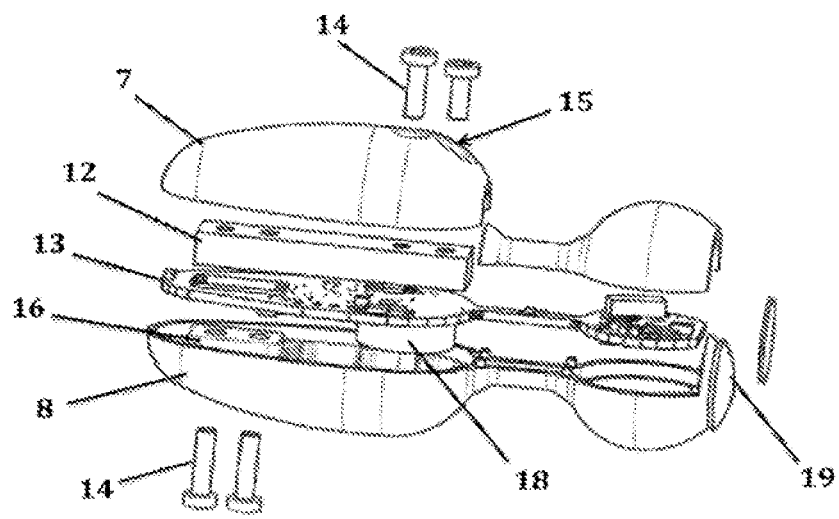
FIG. 4 is a schematic exploded perspective view of the body of the embodiment of the device of FIG. 1.

The body 2, or for a device 6 comprising several parts, at least the part of the body having to be located in the bodily cavity, namely the first part 4 of the body 2, comprises, or is made from, two hollow half-shells 7 and 8, forming an upper part and a lower part of said body 2 or said first part 4 of the body 2, and which are preferably hollow or partially hollow. Preferably, the two half-shells 7 and 8 also comprise, and respectively form, the upper part and the lower part of the second part 5 and the intermediate part 6 of the body 2 (FIG. 4).

The two half-shells 7 and 8 have a shape and dimensions that are adapted to and compatible with the shape and the dimensions of the bodily cavity or cavities in which the body 2 must be positioned. Preferably, the two half-shells 7 and 8 have the same shape and the same dimensions; however, it is conceivable for the two half-shells 7 and 8 to have a different shape.

For example, and if the bodily cavity is the vagina and/or the anal cavity, the two half-shells 7 and 8 have the same shape, so that the body 2, or at least the first part 4 of the body 2, has a substantially cylindrical, or spheroid, shape, or has substantially the shape of a sphere, or an ovoid or an ellipsoid shape. A body 2, or first part 4 of the body 2, of ovoid shape (FIGS. 1 to 4), has the advantage of easier insertion and of being more comfortable during the use of the device 1. Nevertheless, it is possible for at least one of the half-shells 7 or 8 to have a convex surface and for it to have a cylindrical or substantially cylindrical, spheroid, ovoid or ellipsoid shape, and for the other half-shell 7 or 8 to have a substantially planar surface. It is also conceivable for one half-shell 7 or 8 to have a cylindrical, spheroid, ellipsoid shape and the other to have an ovoid shape.

As an example and for a bodily cavity that is the vagina, the first part 4 of the body is ovoid with a diameter of the widest part of between 2.5 and 4.0 cm and a length of between 5 and 7 cm, the second part of spheroid shape having a diameter of between 2 and 4 cm, for a total length of the device of between 8 and 11 cm.

In one preferred embodiment of the invention, the two half-shells 7 and 8 come into contact with one another edge to edge. Preferably, they are rigid, while being deformable under the pressure exerted by the muscle(s) whereof the contractions are to be measured, and also resilient.

In another preferred embodiment of the invention, at least one of the two half-shells 7 or 8, advantageously both half-shells 7 and 8, is or are rigid and substantially non deformable under the contraction force of the muscle(s). The one or both half-shell(s) 7 or 8 is or are mounted floating relative to one another. In other words, the edges of the first half-shell 7 do not come into contact with the edges of the second half-shell 8, thus creating a space 9 between the two half-shells 7 and 8. This has the advantage of obtaining a damping space, the travel of which is preferably limited by stops placed on at least one of the half-shells 7 or 8, thus making it possible to prevent an excessive vertical displacement of the half-shells 7 and 8 relative to one another, which could damage the sensor(s) 11.

Likewise, and for the first part 4 of the body 2, it is advantageous to provide that the edges of each half-shell 7 and 8 of this first part 4 do not come into contact with the edge(s) of the intermediate part 6 of the body 2, or of the half-shell 7 or 8 of this intermediate part 6, thus creating a space 10 between the first part 4 and the intermediate part 6 of the body 2. This has the advantage of creating a damping space, which can preferably be limited by stops placed on at least one of the half-shells 7 or 8.

The device 1 further comprises at least one pressure sensor 11, preferably two sensors 11, one per half-shell 7 or 8, positioned inside the body 2.

The sensor(s) 11 are preferably of the weight indicator type.

In specific embodiments of the invention, the sensor(s) 11 comprise(s) a body 12, made from a rigid, but deformable, material, preferably deformable under the action of a pressure exerted by the contraction and/or the relaxation of the muscle(s) of the bodily cavity or cavities. The rigid material can for example be made from or comprise aluminum.

The body 12 comprises two strain gauges measuring the slightest deformations, even infinitesimal, of the body 12 of the sensor 11. Preferably, the strain gauges are positioned on at least the face, advantageously both faces, of the body 12 that experience(s) the deformations resulting from the contraction pressure, thus making it possible, during the deformation of the body 12 under the action of a pressure exerted on one and/or the other face, to measure the elongation of the two gauges, which is a function of the exerted pressure, and/or to measure the return to the resting state of the two gauges after having experienced the elongation, which is a function of the relaxation after the pressure. Preferably, the strain gauges are positioned on the surface of the two opposite faces of the body 12, on either side of the body 12.

This type of sensor 11 has the advantage of being able to detect, and therefore measure, with sensitivity, a compression force applied on any location of the outer surface of the body 2 of the device 1 and at least the first part 4 of the body 2 and/or the relaxation force following the compression.

Preferably, the sensor(s) record(s) the compression and/or relaxation forces at a frequency of between five and fifteen times per second (5 to 15 Hz), advantageously at a frequency of one hundred milliseconds (10 Hz).

The sensor(s) 11 are positioned on, and are in an electrical relationship with, support means 13, for example an electronic board, a board on which the other electronic or electrical components belonging to the device 1 are also fixed or electrically coupled. These support means 13, this electronic board, are preferably positioned substantially centrally relative to the body 2, at a plane P, which can be the joining plane of the half-shells 7 and 8 or the plane of symmetry of the body 2, or in a plane substantially parallel to the plane P (FIG. 3). Preferably, these support means, this electronic board, can extend along the first part 4 or also along the intermediate part 6 and second part 5 of the body 2 (FIG. 3).

The sensor(s) 11 is, or are, in a relationship with the corresponding half-shell 7 or 8, only by means of the connecting means 14.

These connecting means 14 are not, do not comprise and do not implement, one or several fluids, liquids or gases, or air.

These connecting means 14 are rigid, substantially non-compressible or deformable, in any case not compressible or deformable under the contraction and/or relaxation pressure, of the muscle(s) of the bodily cavity or cavities that the device 1 is meant to measure.

These means 14 physically and mechanically, permanently and continuously connect the or each of the half-shells 7 or 8 to the sensor 11, preferably each half-shell 7 and 8 to a sensor 11, or each half-shell 7 or 8 to its sensor 11, and allow the transmission of the force exerted on the surface of one or both half-shells 7 and 8 to the sensor 11 or to each of the sensors 11.

These means 14 comprise, or are made up of, at least one screw, preferably two screws, advantageously made from or comprising rigid plastic or metal, engaging an orifice 15, or through hole, formed in the half-shell(s) 7 and/or 8, and optionally also engaging a tapped part 16 of the half-shell 7 or 8, the means 14 also engaging a tapped orifice 17, which is optionally also a through hole, formed in the body 12 of the sensor(s) 11.

The means 14 and their permanent securing connection with the half-shell(s) 7 and 8 and the sensor(s) 11 have the advantage of not having moving parts, in motion, during the use of the device 1 according to the invention.

Whether the body 2 is rigid and deformable, or the half-shells 7 and 8 are mounted floating relative to one another, the compression force exerted on the body 2 will be transmitted directly to the sensor(s) 11, without disruptions that could be induced by strain movements or displacements of one or both half-shells 7 and 8 relative to one another or the first part 4 of the body 2 with respect to the second part 5 and the intermediate part 6. The device 1, like the measurements done, are more reliable as a result.

The embodiment in which the half-shells are floating has the additional advantage of having a device 1 with improved sensitivity over the entire body 2, in particular on the first part 4 of the body 2, the slightest contraction, and also the slightest relaxation, of the muscle(s) of the bodily cavity or cavities being transmitted directly to the sensor(s) 11. Furthermore, this has the advantage of having a device 1 that is adaptable to the maximal compression forces that can be exerted on the body 2, and therefore adaptable to the bodily cavities and also different users, this adaptation being done by varying the size of the space 9.

The device 1 further comprises means 18 for supplying power to the sensor(s) 11, as well as all of the elements that make up the device 1. These power supply means 18 comprise, or are, a cell or preferably a rechargeable battery.

In the embodiments of the device 1 in which the electricity supply means comprise a rechargeable battery, the device 1 can further comprise means 19 for recharging the battery. These means 19 can be wired or wireless; they can for example implement an induction phenomenon. Preferably, these means 19 are positioned at the end of the body 2, in particular at the end of the second part 5 of the body 2 that is opposite the first part 4.

The power supply means can also comprise, or cooperate with, different sensors or probes making it possible to monitor or ensure the charge or charging of the battery, including a temperature probe in order to avoid overheating during charging of the battery.

The power supply means 18 can also comprise, or cooperate with, means for regulating the electrical voltage delivered to the components of the device 1.

The device 1 further comprises on and off means. Conventionally, this can be a pushbutton, advantageously positioned at the second part 5 of the body 2. However, preferably, these means comprise an accelerometer detecting a certain amplitude of a movement of the device 1 allowing the latter to be turned on. Advantageously, these means comprise time delay means allowing the stopping, or placement in standby mode, of the device 1 after a length of time following the last detected movement of the device 1.

The device 1 can further comprise visual communication means of its on, off, standby state and/or the charge level of the cell or battery. They may comprise, or be made up of, one or several LEDs, optionally with colors, and may be blinking.

Preferably, the device 1 comprises means for pairing with one or several external devices, separate from the device 1 according to the invention. It also comprises wireless communication means, for example Bluetooth® of the "low energy" type, for communication with one or several other devices 1 according to the invention and/or with one or several external devices. These communication means are preferably positioned in the second part 5 of the body 2, the latter being located outside the bodily cavity during the use of the device 1.

The device 1 can further comprise sensors, for example a temperature probe, in order to measure, and monitor over time, the temperature of the bodily cavity in which the device 1 has been introduced.

As previously described, the device 1 can comprise an accelerometer that may be part of the on and off means of the device 1; nevertheless, this accelerometer also makes it possible to connect a pressure and/or relaxation force detected by the pressure sensor(s) 11 with a movement of the bodily cavity and therefore a contraction and/or relaxation of the muscles. This has the advantage of gaining precision in the detection of the contractions and/or relaxations.

The device 1 can further comprise one or several orientation sensors, a gyroscope and a digital compass, optionally coupled with the accelerometer in order to obtain the position of the device 1 in the three spatial dimensions formed by the bodily cavity, and therefore not only to detect a contraction and/or relaxation movement of the muscles, but also to identify its direction in space.

The device 1 may further comprise self-calibration means.

The device 1 may further comprise hardware and/or software means in order to carry out the measuring method, the method for monitoring contractions and/or muscle relaxation and the exercise method according to the present invention. To that end, it may comprise one or several microprocessors, a memory and means for storing programming and/or operating instructions of the device 1.

The device 1 may advantageously be part of an assembly for measuring contractions and/or the relaxation and/or exercise of the muscles of a bodily cavity, which comprises one or several other devices 1 according to the invention, and which further comprises at least one external device with which the device 1 according to the invention communicates.

This external device comprises means for communicating with the device(s) 1 according to the invention, means for communicating with the user of the device(s) 1, and optionally also means of communication, for example using a telephone or Internet network, for communication with an entity remote from the user of the device 1 according to the invention, for example a computer server. The external device further comprises reception means, processing means and interpreting means, for data and measurements coming from, or going to, the device(s) 1. These means can be, or comprise, hardware and/or software means. In particular, this external device may comprise a microprocessor, a receiver able to receive data, a memory, and a graphic user interface, such as a screen, and keys, or a touch screen.

The external device is preferably mobile. It may be a microcomputer or laptop computer, but preferably, it is a mobile communication device, able to communicate via a communication network, telephone- or computer-based, in particular able to communicate via Internet, for example a telephone, smartphone, electronic tablet or any equivalent devices.

The device 1 according to the invention, or the assembly for measuring contractions and/or the relaxation of the muscles to which it belongs, is preferably used to measure the contractions and/or the relaxation of the muscles forming, or comprised in, a bodily cavity, this bodily cavity advantageously being a vagina or the anal cavity. The device 1 makes it possible to measure the speed and/or the amplitude at which the contractions or the relaxations are done. The device 1 can also be used to monitor, over time, the contractions and/or the relaxation of such muscles, to exercise them or strengthen them.

Preferably, the device 1 according to the invention, or the assembly for measuring contractions and/or the relaxation of the muscles to which it belongs, is used to provide the user of said device 1 or said assembly with information on the contractions and/or the relaxation of the muscles being observed, information, preferably delivered by the external device, that can be visual and for example take the form of one or several written or graphic messages, or auditory messages.

The method according to the invention for measuring the natural contraction, without prior external stimulation, in particular coming from the device 1 according to the invention, and/or the relaxation of the muscles of a bodily cavity, comprises implementing one or several devices 1 according to the invention or the measuring assembly according to the invention.

The measuring method comprises turning on the device(s) 1 according to the invention and the user placing it or them in a bodily cavity; then identifying the occurrence, before a series of subsequent measurements, of a first maximal contraction; measuring its amplitude and/or duration, and/or the maximal relaxation following this first contraction; measuring its amplitude and/or duration, which makes it possible to provide an indication of the performance of the muscle(s) in question. The method next continues with the identification of the occurrence of subsequent contractions and/or subsequent relaxations, and the measurement, over time, of their amplitude and/or duration and/or frequency. The amplitude and/or duration of the first maximal contraction and/or the first maximal relaxation, and the amplitude and/or duration and/or frequency of the subsequent contractions and/or subsequent relaxations, form the measurement data, which are communicated and displayed, preferably in real time, for the user, and which are also recorded in the measuring device(s) 1 or the external mobile device of the measuring assembly.

The step for measuring data of the first maximal contraction and/or the first maximal relaxation can be done automatically as of the occurrence of the first contraction and/or the first relaxation following the placement of the device(s) 1, at the initiative of the user, or in the case of an implementation of the measuring assembly according to the invention, in response to a request for muscle contraction and/or relaxation coming from the external mobile device. Likewise, the user of the device(s) 1, or the measuring assembly according to the invention, is at the initiative of the occurrence, number and frequency of muscle contractions and/or relaxations. However, it is also possible to consider that the external mobile device may request the contractions and/or the relaxations, their number and their frequency, through written, graphic or auditory messages sent to the user.

In the preferred embodiment of the measuring method implementing the measuring assembly according to the invention, the communication and data display step is done by the external mobile device(s).

The measuring method according to the invention can comprise a step for communication by the device(s) 1 of its or their operating state, namely whether it is on or off, the charge level of their power supply means, and the pairing and/or communication state with one or several external devices 1.

The measuring method can further comprise steps prior to the placement of the device(s), which can be carried out alone or in combination with one another, and which consist of:

communicating a user manual for the device(s) 1 and/or the external device to the user;

verifying the physical integrity of the device(s) 1 according to the invention, preferably also verifying the tightness of the coating 3 covering the body 2 of the device;

ensuring the charge level of the power supply means 18 of the device(s) 1, and if necessary, recharging them;

calibrating the device(s) 1 according to the invention outside the bodily cavity or cavities, in order to determine the internal noise induced by the operation of the device(s) 1, or determining an average value representative of this noise, which is advantageously stored in the external device for subsequent use during the measurements of the contractions or the processing of these measurements. Preferably, this calibration is done during recharges of the power supply means 18 in the embodiment of the invention in which these means 18 comprise a rechargeable battery;

correcting, owing to the calibration(s) of the device 1, the measurement errors by smoothing the signals of the measurements, optionally detecting and deleting incorrect measurements.

The measuring method according to the invention can further comprise a step for calibrating, or standardizing, the device(s) 1 according to the invention during their presence in the bodily cavity. Preferably, this calibration is done during a short time period, in the order of several milliseconds to several seconds at most, and advantageously it is done at the end of the placement of the device(s) 1 in the bodily cavity. This step makes it possible to determine: the residual operating bodily noise of the device(s), the noise resulting from the involuntary contractions that may interfere with the identification and/or the measurements of the voluntary contractions for a subsequent use during the measurements of the contractions or the processing of these measurements, and lastly, the detection threshold of a contraction and/or a relaxation.

The measuring method according to the invention may comprise a step for taking account of the values, or average values, of the noises previously described, in order to refine the real-time measurements of the voluntary contractions and/or relaxations by the user.

The method for monitoring the contraction of the muscles of a bodily cavity according to the invention comprises the implementation of the method for measuring the contraction and/or the relaxation of the muscles, which has been previously described.

The method for monitoring the contraction and/or the relaxation of the muscles comprises comparing measuring data collected using the measuring method according to the invention with the data for the first maximal contraction and/or the first maximal relaxation, for a same series of measurements or the comparison with the data for the first maximal contractions and/or maximal relaxations of preceding series of measurements from a measurement history or average values of these preceding measurements, recorded or stored in the device 1 according to the invention or in the external mobile device. This comparison can be done a posteriori, that is to say, after the end of a series of measurements of contractions and/or relaxations, but preferably, it is done in real time during a series of measurements. Preferably, for this comparison of the data, the monitoring method implements the recording of the data on contractions and/or relaxation, either in the device(s) 1, or in the external mobile device.

The monitoring method according to the invention may comprise a step for communicating one or several graphic representations of the results from the comparison of the data to the user. It may also provide a step for producing, and communicating to the user, an overview of the contractions and/or the muscle relaxation over time, for a series of measurements of the contractions and/or relaxation, taking account of the history of several prior measurements, and/or communicating a fatigue level of the muscle(s) in question.

The exercise method according to the invention comprises implementing the method for measuring contractions and/or relaxation, or the method for monitoring the contraction and/or the relaxation of the muscles according to the invention.

Like in the method for measuring contractions and/or muscle relaxations, in the exercise method, the user can initiate the contractions and/or relaxations, and their number, amplitude and frequency. Preferably, and in the case of an implementation of the measuring assembly according to the invention, the contractions and/or the relaxations are done in response to a request for muscle contractions and/or muscle relaxation originating from the external mobile device. To that end, the external mobile device communicates one or several requests for contractions and/or relaxations to the user, as well as goals to be achieved over time, in the form of one or several written, graphic or auditory messages, for example by displaying a graphic representation of a gauge with a contraction and/or relaxation amplitude limit to be reached, which shows one or several data for the first maximal contraction and/or the first maximal relaxation, or one or several subsequent contractions and/or subsequent relaxations, or the level, in real time, of the force of the contraction and/or the relaxation in progress.

Preferably, the request(s) for contractions and/or relaxation of the exercise method, its or their amplitude, duration, number and/or frequency, take(s) account of the data of the first maximal contraction and/or the first maximal relaxation of the measuring method, and the muscle fatigue of the user identified by the monitoring method according to the invention. Preferably, the amplitude and/or the number and/or the frequency of the requested contractions and/or relaxations is or are adapted, advantageously adjusted in real time, as a function of the maximal contraction and/or the maximal relaxation recorded for the first muscle contraction and/or the first relaxation, and/or the subsequent muscle contraction and/or subsequent relaxation evolution, relative to this maximal contraction and/or a maximal relaxation.

The measuring method and/or the monitoring method and/or the exercise method according to the invention can comprise a step for communication by the measuring device 1 according to the invention, or the external mobile device, with a remote third party, an entity remote from the user of the device 1 according to the invention, for example a computer server, through a communication network, for example telephone-based, or over the Internet. This step can comprise the communication to the user of information useful for the implementation of the methods according to the invention, or relative to the bodily cavity and/or the muscles of which it is composed. For example, the method(s) can comprise a step for communicating one or several indications on the preparation and/or the execution of one or several contractions, communication of indicators, for example representative of muscle performance, endurance, reflexes and/or control of the contractions, the success or failure of an exercise, the execution time of the monitoring of the muscle contraction, or the exercise performed.

The invention claimed is:

1. A device for measuring contractions and/or relaxation of one or several muscles of a body cavity, the device comprising:

a hollow body (i) configured to be positioned in the body cavity, (ii) being covered by a coating made of at least a biocompatible material, and (iii) being formed by a first half-shell and a second half-shell; and at least one pressure sensor in the hollow body; wherein:
the first half-shell and the second half-shell are physically connected, permanently and continuously, using non-compressible or deformable connecting means, to the at least one pressure sensor; and
the first half-shell, the second half-shell and the at least one pressure sensor are configured such that the at least one pressure sensor is between the first half-shell and the second half-shell so that each of the first half-shell and the second half-shell directly contacts the at least one pressure sensor and is directly connected to the at least one pressure sensor by the non-compressible or deformable connecting means but does not directly contact another of the first half-shell and the second half-shell; and
the first half-shell and the second half-shell are only connected via the at least one pressure sensor.

2. The device according to claim 1, wherein the connecting means of the two half-shells to the at least one pressure sensor includes at least one screw, engaging both of the half-shells and the sensor.

3. The device according to claim 1, wherein the first half-shell and the second half-shell are mounted floating relative to one another, and edges of the first half-shell do not contact edges of the second half-shell, which forms a space between the edges of the first half-shell and the second half-shell.

4. The device according to claim 1, further comprising two pressure sensors, which includes the at least one pressure sensor, and each of the two pressure sensors is coupled, by separate connecting means, to one half-shell of the first half-shell and the second half-shell.

5. The device according to claim 1, wherein the at least one pressure sensor is a weight indicator type and includes a body made from aluminum and two strain gauges on two opposite surfaces of the body.

6. The device according to claim 1, further comprising wireless communication means with an external mobile device.

7. The device according to claim 1, wherein the body includes a first part configured to be located, during the use of the device, in the body cavity, which is ovoid, a second part configured to be located, during the use of the device, outside the body cavity, with a spheroid shape, and the first and the second parts are coupled by an intermediate part with a cylindrical shape.

8. A measuring assembly for monitoring contractions and/or relaxation and exercise of muscles forming, or comprised in, the body cavity, the measuring assembly comprising one or more measuring devices according to claim 1, and one or more external mobile devices communicating with the one or more measuring devices.

9. The assembly according to claim 8, wherein the one or more external mobile devices include means of communication with a user of the one or more measuring devices, and means of communication using a telephone or Internet communication network for communication with a remote third party.

10. A method for measuring contraction and/or relaxation of muscles of the body cavity of a user, the method comprising the following steps:
providing one or more measuring devices according to claim 1,
starting the one or more measuring devices,
placing the one or more measuring devices in the body cavity of the user comprising or being formed by muscles,
identifying and measuring an amplitude and/or a duration of a first maximal contraction and/or a first maximal relaxation of the muscles,
identifying and measuring, over time, the amplitude and/or the duration and/or a frequency of one or more subsequent contractions and/or subsequent relaxations, the amplitude and/or the duration of the first maximal contraction and/or the first maximal relaxation and the amplitude and/or the duration and/or the frequency of the subsequent contractions and/or the subsequent relaxations constituting measurement data, and
communicating and displaying, in real time, the measurement data to the user.

11. The measuring method according to claim 10, further comprising a step of communicating, by the one or more measuring devices of an operating state of the one or more measuring devices, and/or a step of calibrating the one or more measuring devices before and/or after the one or more measuring devices are placed in the body cavity.

12. A method for monitoring the contraction and/or the relaxation of the muscles of the body cavity comprising steps of:
implementing the measuring method according to claim 10, and
comparing measuring data, collected over time using the measuring method, with (i) the measurement data of the first maximal contraction and/or the first maximal relaxation, for a same series of measurements, or (ii) the measurement data of the first maximal contractions and/or maximal relaxations of preceding series of measurements from a measurement history or one or more average values of the first maximal contractions and/or the maximal relaxations of the preceding measurements, and obtaining results of the comparison.

13. The monitoring method according to claim 12, further comprising a step of communicating, to the user, one or more written, graphic and/or auditory representations of the results from the comparing step.

14. A method for exercising muscles of the body cavity, the method comprising:
implementing the measuring method according to claim 10, and
adapting the amplitude and/or the duration and/or a number and/or the frequency of the contractions and/or the relaxations done by, or requested from, the user as a function of the measurement data from the first maximal contraction and/or the first maximal relaxation and/or muscle fatigue of the user.

15. The measuring method according to claim 10, further comprising a step for communication by the one or more measuring devices, or an external mobile device, with a third party remote from the user in order to prepare and/or execute one or more of the steps of measuring, monitoring and/or exercise methods, or for the communication of indicators representative of muscle performance of the user.

16. A method for measuring contraction and/or relaxation of muscles of the body cavity of a user, the method comprising the following steps:
providing the assembly according to claim 8,
starting the one or more measuring device,
placing the one or more measuring device in the body cavity of the user comprising or being formed by muscles,
identifying and measuring an amplitude and/or a duration of a first maximal contraction and/or a first maximal relaxation of the muscles, identifying and measuring, over time, the amplitude and/or the duration and/or a frequency of one or more subsequent contractions and/or subsequent relaxations, the amplitude and/or the duration of the first maximal contraction and/or the first maximal relaxation and the amplitude and/or the duration and/or the frequency of the subsequent contractions and/or the subsequent relaxations constituting measurement data, and communicating and displaying, in real time, the measurement data to the user.

17. The measuring method according to claim 12, further comprising a step for communication by the one or more measuring devices, or an external mobile device, with a third party remote from the user in order to prepare and/or execute one or more of the steps of measuring, monitoring and/or exercise methods, or for the communication of indicators representative of muscle performance of the user.

* * * * *